(12) United States Patent
Zhao et al.

(10) Patent No.: US 9,399,129 B2
(45) Date of Patent: Jul. 26, 2016

(54) MRI COMPATIBLE IMPLANTABLE MEDICAL LEAD AND METHOD OF MAKING SAME

(75) Inventors: Yong D. Zhao, Simi Valley, CA (US); Xiaoyi Min, Thousand Oaks, CA (US); Virote Indravudh, Santa Clarita, CA (US)

(73) Assignee: PACESETTER, INC., Sylmar, CA (US)

( * ) Notice: Subject to any disclaimer, the term of this patent is extended or adjusted under 35 U.S.C. 154(b) by 1674 days.

(21) Appl. No.: 12/262,083

(22) Filed: Oct. 30, 2008

(65) Prior Publication Data

US 2010/0114277 A1    May 6, 2010

(51) Int. Cl.
*A61N 1/00* (2006.01)
*A61N 1/05* (2006.01)
*A61N 1/08* (2006.01)

(52) U.S. Cl.
CPC ............ *A61N 1/056* (2013.01); *A61N 2001/086* (2013.01)

(58) Field of Classification Search
CPC .... A61N 1/05; A61N 1/056; A61N 2001/086
USPC .................................. 607/115, 116, 119, 122
See application file for complete search history.

(56) References Cited

U.S. PATENT DOCUMENTS

| | | |
|---|---|---|
| 2007/0112398 A1 | 5/2007 | Stevenson et al. |
| 2008/0132986 A1 | 6/2008 | Gray et al. |
| 2008/0132987 A1 | 6/2008 | Westlund et al. |
| 2008/0161886 A1 | 7/2008 | Stevenson et al. |
| 2008/0243218 A1 | 10/2008 | Bottomley et al. |
| 2008/0262584 A1 * | 10/2008 | Bottomley et al. ........... 607/119 |

FOREIGN PATENT DOCUMENTS

| | | |
|---|---|---|
| WO | 2007102893 A2 | 9/2007 |
| WO | 2007102893 A3 | 9/2007 |

\* cited by examiner

*Primary Examiner* — Mallika D Fairchild (57) ABSTRACT

An implantable medical lead is disclosed herein. The lead may include a body and an electrical pathway. The body may include a distal portion with an electrode and a proximal portion with a lead connector end. The electrical pathway may extend between the electrode and lead connector end and may include a coiled inductor including first and second electrically conductive filar cores. The first and second filar cores may be physically joined into a unified single piece proximal terminal on a proximal end of the coiled inductor. The first and second cores may be physically joined into a unified single piece distal terminal on a distal end of the coiled inductor. The first and second filar cores may be helically wound into a coiled portion between the proximal and distal terminals, the filar cores being electrically isolated from each other in the coiled portion. The proximal terminal may be electrically coupled to a portion of the electrical pathway extending to the lead connector end, and the distal terminal may be electrically coupled to a portion of the electrical pathway extending to the electrode.

27 Claims, 8 Drawing Sheets

MRI COMPATIBLE IMPLANTABLE MEDICAL LEAD AND METHOD OF MAKING SAME

CROSS-REFERENCE TO RELATED APPLICATIONS

This application is related to U.S. patent application Ser. No. 12/262,047, filed concurrently herewith on Oct. 30, 2008, titled "MRI Compatible Implantable Medical Lead and Method of Making Same", now U.S. Pat. No. 8,634,931.

FIELD OF THE INVENTION

The present invention relates to medical apparatus and methods. More specifically, the present invention relates to implantable medical leads and methods of manufacturing such leads.

BACKGROUND OF THE INVENTION

Existing implantable medical leads for use with implantable pulse generators, such as neurostimulators, pacemakers, defibrillators or implantable cardioverter defibrillators ("ICD"), are prone to heating and induced current when placed in the strong magnetic (static, gradient and RF) fields of a magnetic resonance imaging ("MRI") machine. The heating and induced current are the result of the lead acting like an antenna in the magnetic fields generated during a MRI. Heating and induced current in the lead may result in deterioration of stimulation thresholds or, in the context of a cardiac lead, even increase the risk of cardiac tissue damage and perforation.

Over fifty percent of patients with an implantable pulse generator and implanted lead require, or can benefit from, a MRI in the diagnosis or treatment of a medical condition. MRI modality allows for flow visualization, characterization of vulnerable plaque, non-invasive angiography, assessment of ischemia and tissue perfusion, and a host of other applications. The diagnosis and treatment options enhanced by MRI are only going to grow over time. For example, MRI has been proposed as a visualization mechanism for lead implantation procedures.

There is a need in the art for an implantable medical lead configured for improved MRI safety. There is also a need in the art for methods of manufacturing and using such a lead.

BRIEF SUMMARY OF THE INVENTION

An implantable medical lead is disclosed herein. In one embodiment, the lead includes a body and an electrical pathway. The body may include a distal portion with an electrode and a proximal portion with a lead connector end. The electrical pathway may extend between the electrode and lead connector end and may include a coiled inductor including first and second electrically conductive filar cores. The first and second filar cores may be physically joined into a unified single piece proximal terminal on a proximal end of the coiled inductor. The first and second cores may be physically joined into a unified single piece distal terminal on a distal end of the coiled inductor. The first and second filar cores may be helically wound into a coiled portion between the proximal and distal terminals, the filar cores being electrically isolated from each other in the coiled portion. The proximal terminal may be electrically coupled to a portion of the electrical pathway extending to the lead connector end, and the distal terminal may be electrically coupled to a portion of the electrical pathway extending to the electrode.

An implantable medical lead is disclosed herein. In one embodiment, the lead may include a lead body, an electrical pathway, and a coiled inductor. The lead body may include an electrode at a distal portion of the lead body and a lead connector end at a proximal portion of the lead body. The electrical pathway may extend between the electrode and the lead connector end. The coiled inductor may form a segment of the electrical pathway and may be formed of multiple filars helically wound to form a coiled portion of the coiled inductor. The multiple filars may be electrically insulated from each other along the coiled portion and physically electrically contacting at proximal and distal ends of the multiple filars.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Disclosed herein is an implantable medical lead 10 employing a lumped inductor 160 near the distal end 45 of the lead 10. In one embodiment, the lumped inductor 160 is a coil inductor 160 that may be a uni-filar single layer coil inductor 160a. To provide advantages not offered by the uni-filar single layer coil inductor 160a, the lumped inductor 160 is a coil inductor 160 that may be bi-filar single layer coil inductor 160b, 160c or a bi-filar multi-layer coil inductor 160d. The advantages provided by the bi-filar single layer coil inductor 160b, 160c and the bi-filar multi-layer coil inductor 160d include, among others, reduced DC resistance, increased heat conduction efficiency, circuit redundancy, large inductance at common MRI operating frequencies, and small size allowing the coil conductor 160 to be employed in 6F or smaller leads.

Figure 1:
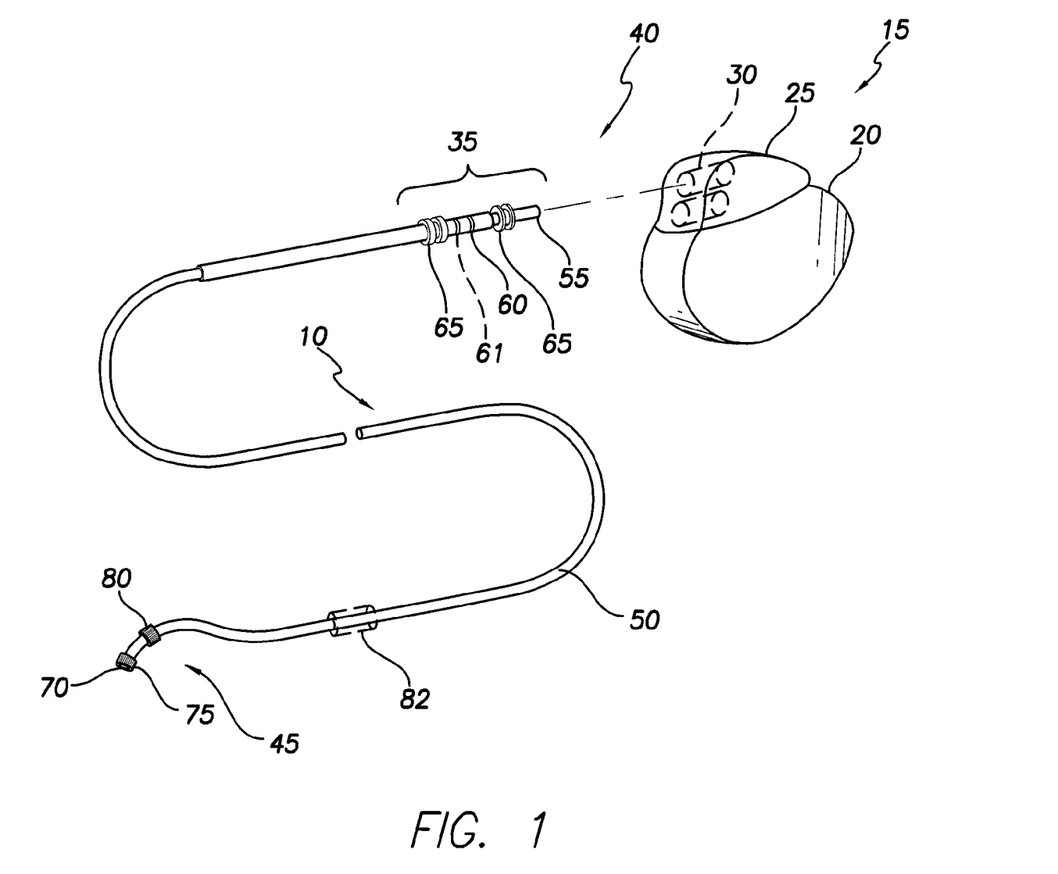
FIG. 1 is an isometric view of an implantable medical lead and a pulse generator for connection thereto.

For a general discussion of an embodiment of a lead 10 employing the coil inductor 160, reference is made to FIG. 1, which is an isometric view of the implantable medical lead 10 and a pulse generator 15 for connection thereto. The pulse generator 15 may be a pacemaker, defibrillator, ICD or neurostimulator. As indicated in FIG. 1, the pulse generator 15 may include a can 20, which may house the electrical components of the pulse generator 15, and a header 25. The header may be mounted on the can 20 and may be configured to receive a lead connector end 35 in a lead receiving receptacle 30.

As shown in FIG. 1, in one embodiment, the lead 10 may include a proximal end 40, a distal end 45 and a tubular body 50 extending between the proximal and distal ends. In some embodiments, the lead may be a 6 French, model 1688T lead, as manufactured by St. Jude Medical of St. Paul, Minn. In other embodiments, the lead may be a 6 French model 1346T lead, as manufactured by St. Jude Medical of St. Paul, Minn. In other embodiments, the lead 10 may be of other sizes and models. The lead 10 may be configured for a variety of uses. For example, the lead 10 may be a RA lead, RV lead, LV Brady lead, RV Tachy lead, intrapericardial lead, etc.

As indicated in FIG. 1, the proximal end 40 may include a lead connector end 35 including a pin contact 55, a first ring contact 60, a second ring contact 61, which is optional, and sets of spaced-apart radially projecting seals 65. In some embodiments, the lead connector end 35 may include the same or different seals and may include a greater or lesser number of contacts. The lead connector end 35 may be received in a lead receiving receptacle 30 of the pulse generator 15 such that the seals 65 prevent the ingress of bodily fluids into the respective receptacle 30 and the contacts 55, 60, 61 electrically contact corresponding electrical terminals within the respective receptacle 30.

As illustrated in FIG. 1, in one embodiment, the lead distal end 45 may include a distal tip 70, a tip electrode 75 and a ring electrode 80. In some embodiments, the lead body 50 is configured to facilitate passive fixation and/or the lead distal end 45 includes features that facilitate passive fixation. In such embodiments, the tip electrode 75 may be in the form of a ring or domed cap and may form the distal tip 70 of the lead body 50.

Figure 2:
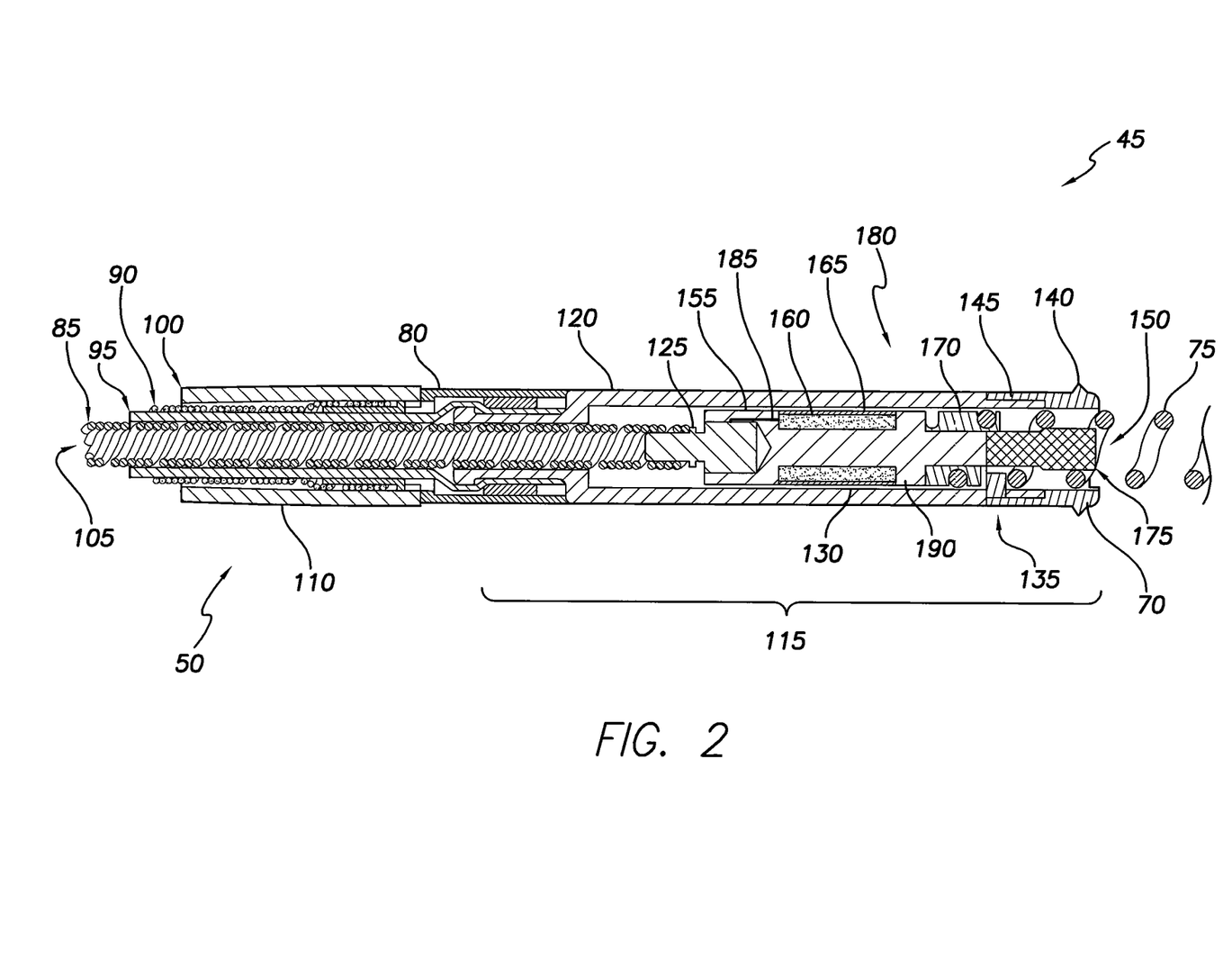
FIG. 2 is a longitudinal cross-section of the lead distal end.

As shown in FIG. 2, which is a longitudinal cross-section of the lead distal end 45, in some embodiments, the tip electrode 75 may be in the form of a helical anchor 75 that is extendable from within the distal tip 70 for active fixation and serving as a tip electrode 75.

As shown in FIG. 1, in some embodiments, the distal end 45 may include a defibrillation coil 82 about the outer circumference of the lead body 50. The defibrillation coil 82 may be located proximal of the ring electrode 70.

The ring electrode 80 may extend about the outer circumference of the lead body 50, proximal of the distal tip 70. In other embodiments, the distal end 45 may include a greater or lesser number of electrodes 75, 80 in different or similar configurations.

As can be understood from FIGS. 1 and 2, in one embodiment, the tip electrode 75 may be in electrical communication with the pin contact 55 via a first electrical conductor 85, and the ring electrode 80 may be in electrical communication with the first ring contact 60 via a second electrical conductor 90. In some embodiments, the defibrillation coil 82 may be in electrical communication with the second ring contact 61 via a third electrical conductor. In yet other embodiments, other lead components (e.g., additional ring electrodes, various types of sensors, etc.) (not shown) mounted on the lead body distal region 45 or other locations on the lead body 50 may be in electrical communication with a third ring contact (not shown) similar to the second ring contact 61 via a fourth electrical conductor (not shown). Depending on the embodiment, any one or more of the conductors 85, 90 may be a multi-strand or multi-filar cable or a single solid wire conductor run singly or grouped, for example in a pair.

As shown in FIG. 2, in one embodiment, the lead body 50 proximal of the ring electrode 80 may have a concentric layer configuration and may be formed at least in part by inner and outer helical coil conductors 85, 90, an inner tubing 95, and an outer tubing 100. The helical coil conductor 85, 90, the inner tubing 95 and the outer tubing 100 form concentric layers of the lead body 50. The inner helical coil conductor 85 forms the inner most layer of the lead body 50 and defines a central lumen 105 for receiving a stylet or guidewire therethrough. The inner helical coil conductor 85 is surrounded by the inner tubing 95 and forms the second most inner layer of the lead body 50. The outer helical coil conductor 90 surrounds the inner tubing 95 and forms the third most inner layer of the lead body 50. The outer tubing 100 surrounds the outer helical coil conductor 90 and forms the outer most layer of the lead body 50.

In one embodiment, the inner tubing 95 may be formed of an electrical insulation material such as, for example, ethylene tetrafluoroethylene ("ETFE"), polytetrafluoroethylene ("PTFE"), silicone rubber, silicone rubber polyurethane copolymer ("SPC"), or etc. The inner tubing 95 may serve to electrically isolate the inner conductor 85 from the outer conductor 90. The outer tubing 100 may be formed of a biocompatible electrical insulation material such as, for example, silicone rubber, silicone rubber-polyurethane-copolymer ("SPC"), polyurethane, gore, or etc. The outer tubing 100 may serve as the jacket 100 of the lead body 50, defining the outer circumferential surface 110 of the lead body 50.

As illustrated in FIG. 2, in one embodiment, the lead body 50 in the vicinity of the ring electrode 80 transitions from the above-described concentric layer configuration to a header assembly 115. For example, in one embodiment, the outer tubing 100 terminates at a proximal edge of the ring electrode 80, the outer conductor 90 mechanically and electrically couples to a proximal end of the ring electrode 80, the inner tubing 95 is sandwiched between the interior of the ring electrode 80 and an exterior of a proximal end portion of a body 120 of the header assembly 115, and the inner conductor 85 extends distally past the ring electrode 80 to electrically and mechanically couple to components of the header assembly 115 as discussed below.

As depicted in FIG. 2, in one embodiment, the header assembly 115 may include the body 120, a coupler 125, an inductor assembly 130, and a helix assembly 135. The header body 120 may be a tube forming the outer circumferential surface of the header assembly 115 and enclosing the components of the assembly 115. The header body 120 may have a soft atraumatic distal tip 140 with a radiopaque marker 145 to facilitate the soft atraumatic distal tip 140 being visualized during fluoroscopy. The distal tip 140 may form the extreme distal end 70 of the lead 10 and includes a distal opening 150 through which the helical tip anchor 75 may be extended or retracted. The header body 120 may be formed of polyetheretherketone ("PEEK"), polyurethane, or etc., the soft distal tip 140 may be formed of silicone rubber, SPC, or etc., and the radiopaque marker 145 may be formed of platinum, platinum-iridium alloy, tungsten, tantalum, or etc.

As indicated in FIG. 2, in one embodiment, the inductor assembly 130 may include a bobbin 155, a coil inductor 160 and a shrink tube 165. The bobbin 155 may include a proximal portion that receives the coupler 125, a barrel portion about which the coil inductor 160 is wound, and a distal portion coupled to the helix assembly 135. The bobbin 155 may be formed of an electrical insulation material such as PEEK, polyurethane, or etc.

As illustrated in FIG. 2, the shrink tube 165 may extend about the coil inductor 160 to generally enclose the coil inductor 160 within the boundaries of the bobbin 155 and the shrink tube 165. The shrink tube 165 may act as a barrier between the coil inductor 160 and the inner circumferential surface of the header body 120. Also, the shrink tube 165 may be used to form at least part of a hermitic seal about the coil inductor 160. The shrink tube 165 may be formed of fluorinated ethylene propylene ("FEP"), polyester, or etc.

As shown in FIG. 2, a distal portion of the coupler 125 may be received in the proximal portion of the bobbin 155 such that the coupler 125 and bobbin 155 are mechanically coupled to each other. A proximal portion of the coupler 125 may be received in the lumen 105 of the inner coil conductor 85 at the extreme distal end of the inner coil conductor 85, the inner coil conductor 85 and the coupler 125 being mechanically and electrically coupled to each other. The coupler 125 may be formed of MP35N, platinum, platinum iridium alloy, stainless steel, or etc.

As indicated in FIG. 2, the helix assembly 135 may include a base 170, the helical anchor electrode 75, and a steroid plug 175. The base 170 forms the proximal portion of the assembly 135. The helical anchor electrode 75 forms the distal portion of the assembly 135. The steroid plug 175 may be located within the volume defined by the helical coils of the helical anchor electrode 75. The base 170 and the helical anchor electrode 75 are mechanically and electrically coupled together. The distal portion of the bobbin 155 may be received in the helix base 170 such that the bobbin 155 and the helix base 170 are mechanically coupled to each other. The base 170 of the helix assembly 135 may be formed of platinum, platinum-iridium alloy, MP35N, stainless steel, or etc. The helical anchor electrode 75 may be formed of platinum, platinum-iridium ally, MP35N, stainless steel, or etc.

As illustrated in FIG. 2, a distal portion of the coupler 125 may be received in the proximal portion of the bobbin 155 such that the coupler 125 and bobbin 155 are mechanically coupled to each other. A proximal portion of the coupler 125 may be received in the lumen 105 of the inner coil conductor 85 at the extreme distal end of the inner coil conductor 85 such that the inner coil conductor 85 and the coupler 125 are both mechanically and electrically coupled to each other. The coupler 125 may be formed of MP35N, stainless steel, or etc.

As can be understood from FIG. 2 and the preceding discussion, the coupler 125, inductor assembly 130, and helix assembly 135 are mechanically coupled together such that these elements 125, 130, 135 of the header assembly 115 do not displace relative to each other. Instead these elements 125, 130, 135 of the header assembly 115 are capable of displacing as a unit relative to, and within, the body 120 when a stylet or similar tool is inserted through the lumen 105 to engage the coupler 125. In other words, these elements 125, 130, 135 of the header assembly 115 form an electrode-inductor assembly 180, which can be caused to displace relative to, and within, the header assembly body 120 when a stylet engages the proximal end of the coupler 125. Specifically, the stylet is inserted into the lumen 105 to engage the coupler 125, wherein rotation of the electrode-inductor assembly 180 via the stylet in a first direction causes the electrode-inductor assembly 180 to displace distally, and rotation of the electrode-inductor assembly 180 via the stylet in a second direction causes the electrode-inductor assembly 180 to retract into the header assembly body 120. Thus, causing the electrode-inductor assembly 180 to rotate within the body 120 in a first direction causes the helical anchor electrode 75 to emanate from the tip opening 150 for screwing into tissue at the implant site. Conversely, causing the electrode-inductor assembly 180 to rotate within the body 120 in a second direction causes the helical anchor electrode 75 to retract into the tip opening 150 to unscrew the anchor 75 from the tissue at the implant site.

As already mentioned and indicated in FIG. 2, the coil inductor 160 may be wound about the barrel portion of the bobbin 155. A proximal end 185 of the coil inductor 160 may extend through the proximal portion of the bobbin 155 to electrically couple with the coupler 125, and a distal end 190 of the coil inductor 160 may extend through the distal portion of the bobbin 155 to electrically couple to the helix base 170. Thus, in one embodiment, the coil inductor 160 is in electrical communication with the both the inner coil conductor 85, via the coupler 125, and the helical anchor electrode 75, via the helix base 170. Therefore, the coil inductor 160 acts as an electrical pathway through the electrically insulating bobbin 155 between the coupler 125 and the helix base 170. In one embodiment, all electricity destined for the helical anchor electrode 75 from the inner coil conductor 85 passes through the coil inductor 160 such that the inner coil conductor 85 and the electrode 75 both benefit from the presence of the coil inductor 160, the coil inductor 160 acting as a lumped inductor 160 when the lead 10 is present in a magnetic field of a MRI.

As the helix base 170 may be formed of a mass of metal, the helix base 170 may serve as a relatively large heat sink for the inductor coil 160, which is physically connected to the helix base 170. Similarly, as the coupler 125 may be formed of a mass of metal, the coupler 125 may serve as a relatively large heat sink for the inductor coil 160, which is physically connected to the coupler 125.

Figure 3:
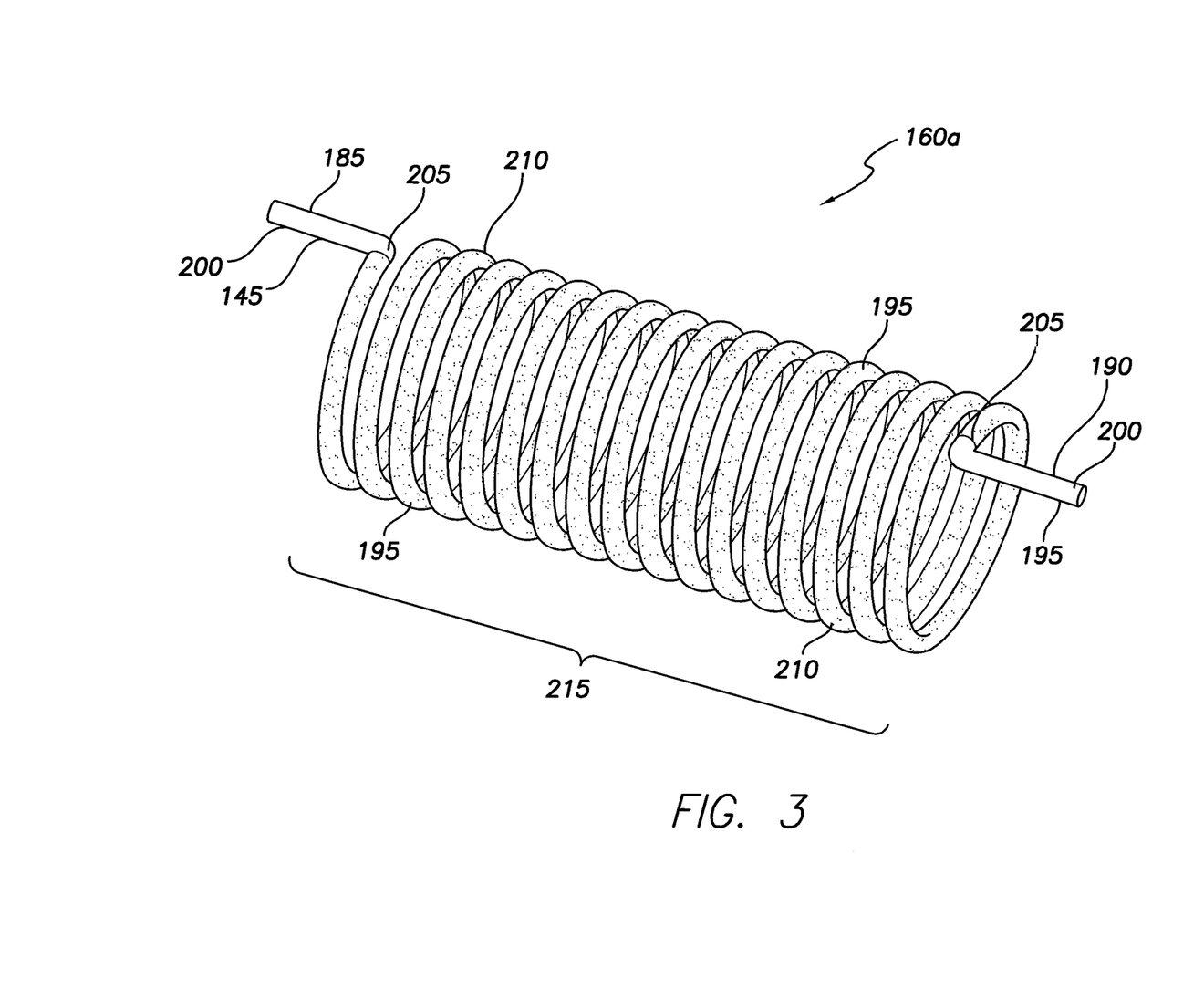
FIG. 3 is an isometric view of a uni-filar single layer coil inductor.

The coil inductor 160 may have a variety of winding configurations. For example, as indicated in FIG. 3, which is an isometric view of one example coil inductor configuration, the coil inductor 160 may be a uni-filar single layer coil inductor 160a formed of a helically wound single filar 195 having an electrically conductive core 200 and an electrical insulation layer 205. The helically wound filar 195 forms a plurality of coils 210, which form the coiled portion 215 of the coil inductor 160a. The coil 210 may define a center cylindrical space that receives the barrel portion of the bobbin 155 when the coil inductor 160a is wound about the barrel portion of the bobbin 155, as indicated in FIG. 2.

As illustrated in FIG. 3, the helically wound filar 195 terminates on the proximal and distal ends of the coil inductor 160a as proximal and distal straight filar segments 185, 190, which extend through the respective proximal and distal portions of the bobbin 155 to respectively electrically couple to the coupler 125 and the helix base 170, as discussed above with respect to FIG. 2. The extent of the filar 195 extending through the coils 210 of the coiled portion 215 is jacketed by the electrical insulation layer 205, and the extent of the filar 195 forming the proximal and distal straight segments 185, 190 is un-insulated such that the electrically conductive core 200 is exposed.

The uni-filar single layer coil inductor 160a discussed above with respect to FIG. 3 may operate as a lumped inductor 160 for a lead 10 to reduce RF heating during a MRI scan. The uni-filar single layer coil inductor 160a may generate high impedance to resist induced RF current at selected high frequencies common to most MRI scans, such as, for example, 64 MHz for a 1.5 T MRI scanner and 128 MHz for a 3.0 T MRI scanner. The uni-filar single layer coil inductor 160a does not impact the pacing or sensing circuit in the lead 10 when the working frequency is less than approximately 1 KHz, resulting in a low-pass filter.

However, there are a number of shortcomings associated with the above-discussed uni-filar single layer coil inductor 160a. For example, the uni-filar construction of the coil inductor 160a does not provide pacing circuit redundancy, unlike the multi-filar coils or cables employed for the pacing conductors 85, 90 of the lead 10. Also, the uni-filar single layer coil inductor 160a results in a large DC resistance and poor heat conduction due to the singe filar 195, which has a long route and a small diameter. Finally, to achieve a coil inductor 160 with the appropriate self resonant frequency ("SRF") for specific MRI frequencies, such as, for example, 64 MHz for a 1.5 T MRI scan, a uni-filar coil inductor should have five layers as opposed to a single layer, causing the coil inductor outside diameter to be larger than may be accommodated in a 6F lead.

To address the shortcomings associated with the above-discussed uni-filar single layer coil inductor 160a or a uni-filar multi-layer coil inductor, a lumped inductor 160 may be provided for the lead 10 wherein the lumped inductor 160 employs a multi-filar configuration similar to the single layer multi-filar coil inductors 160b, 160c discussed below with respect to FIGS. 4 and 5 or the multi-layer multi-filar coil inductor 160d discussed below with respect to FIGS. 6 and 7.

Figure 4:
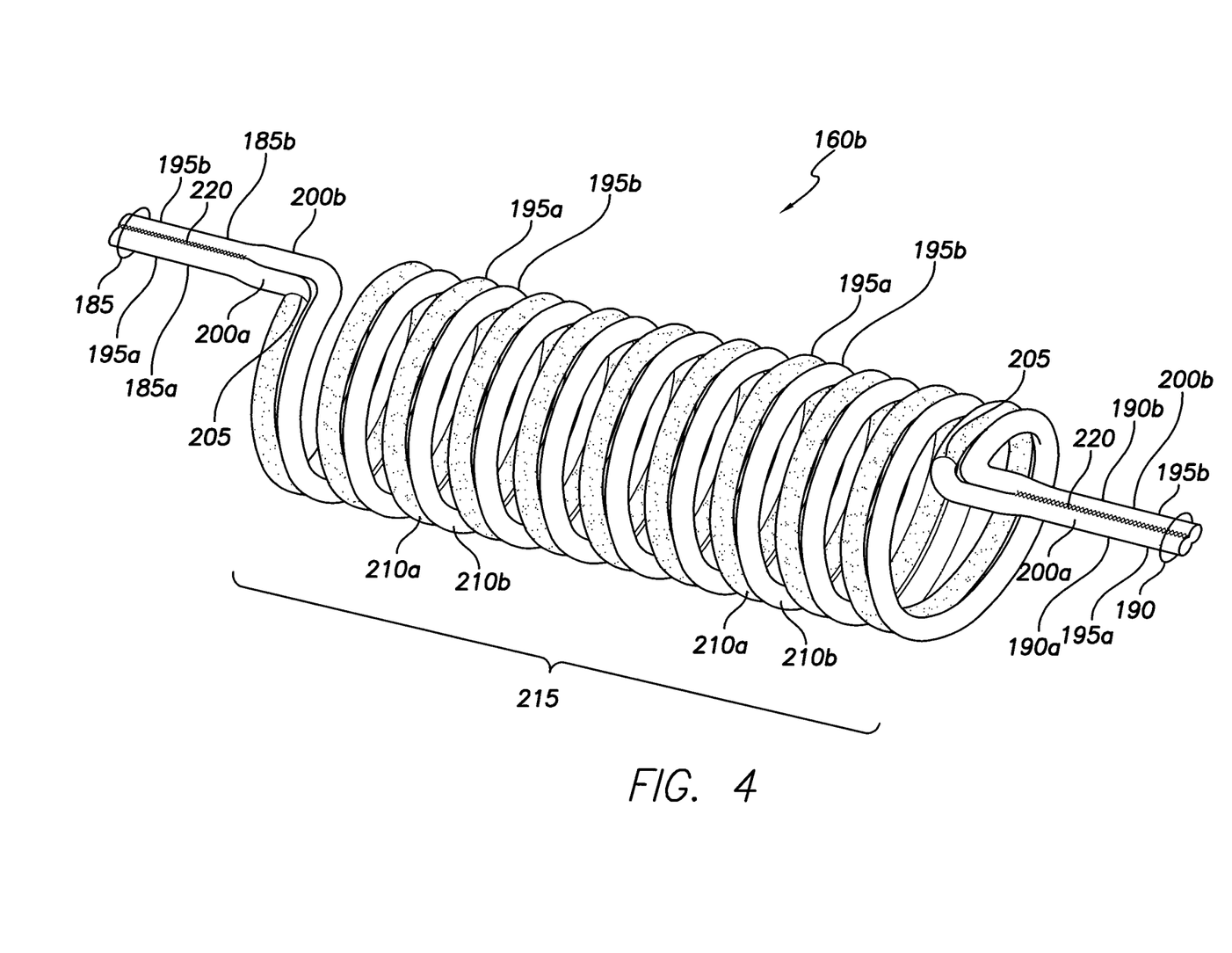
FIG. 4 is an isometric view of a bi-filar single layer coil inductor having only one of its pair of filars provided with an electrically insulating jacket.

As depicted in FIG. 4, which is an isometric view of a multi-filar coil inductor configuration, the coil inductor 160 may be a bi-filar single layer coil inductor 160b formed of a pair of helically wound filars 195a, 195b. Each helically wound filar 195a, 195b has an electrically conductive core 200a, 200b. However, only one of the filars 195a has an electrical insulation layer 205, the other filar 195b being completely free of an electrical insulation layer 205.

As shown in FIG. 4, the pair of helically wound filars 195a, 195b form a plurality of coils 210a, 210b, which form the coiled portion 215 of the coil inductor 160b. The coils 210a, 210b may define a center cylindrical space that receives the barrel portion of the bobbin 155 when the coil inductor 160b is wound about the barrel portion of the bobbin 155, as indicated in FIG. 2.

As illustrated in FIG. 4, each helically wound filar 195a, 195b terminates on the proximal end of the coil inductor 160b as proximal straight filar segments 185a, 185b, which are joined together via joining material 220, for example, a weld, solder, braze or electrically conductive epoxy, to form a unified single-piece proximal straight filar segment 185. Similarly, each helically wound filar 195a, 195b terminates on the distal end of the coil inductor 160b as distal straight filar segments 190a, 190b, which are joined together via joining material 220, for example, a weld, solder, braze or electrically conductive epoxy, to form a unified single-piece distal straight filar segment 190. The unified single-piece proximal and distal straight filar segments 185, 190 extend through the respective proximal and distal portions of the bobbin 155 to respectively electrically couple to the coupler 125 and the helix base 170, as discussed above with respect to FIG. 2.

As indicated in FIG. 4, the extent of the insulated filar 195a extending through the coils 210a of the coiled portion 215 is jacketed by the electrical insulation layer 205, and the extent of the insulated filar 195a forming the proximal and distal straight segments 185a, 190a is un-insulated such that the electrically conductive core 200a is exposed. The extent of the un-insulated filar 195b extending through the coils 210b of the coiled portion 215 is free of an electrical insulation layer 205 such that the electrically conductive core 200b is exposed, and the extent of the un-insulated filar 195b forming the proximal and distal straight segments 185b, 190b is un-insulated such that the electrically conductive core 200b is exposed. As the coils 210a, 210b of the insulated filar 195a and un-insulated filar 195b alternate with respect to position in the coiled inductor 160b, the insulation layer 205 of the insulated filar 195a electrically isolates the conductor core 200a of the insulated filar 195a from the conductor core 200b of the un-insulated filar 195b and the conductor core 200b of the un-insulated filar 195b from itself.

The preceding discussion regarding the multi-filar coil inductor 160b depicted in FIG. 4 was given in the context of the multi-filar coil inductor 160b being a bi-filar single layer coil inductor 160b. However, in some embodiments, the multi-filar coil inductor 160b of FIG. 4 may have three filars, four filars or more filars, the filars being helically wound, alternatingly located in the helical coil, joined at their respective proximal and distal straight filar segments, and every other filar being insulated, as discussed above.

Figure 5:
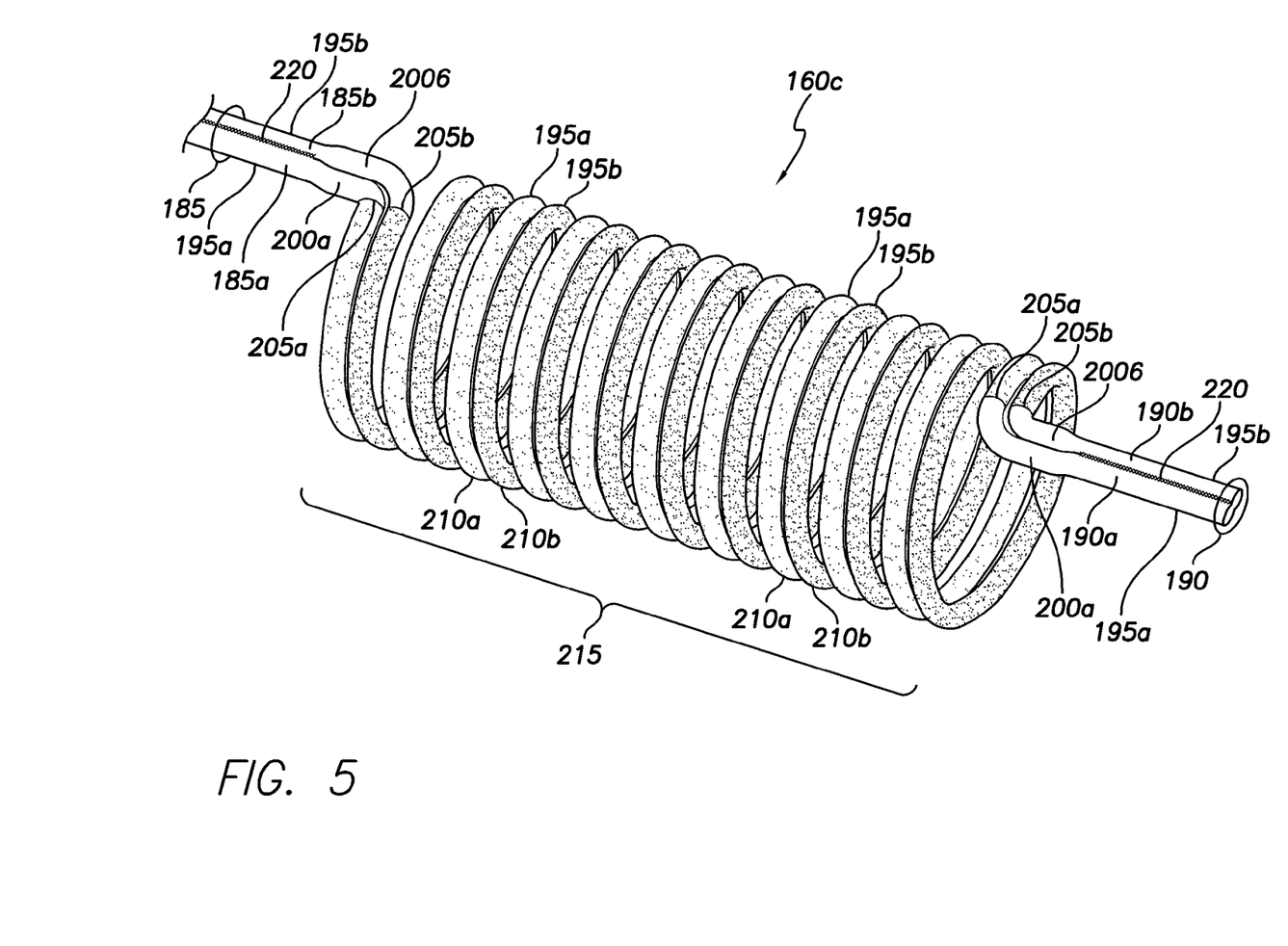
FIG. 5 is an isometric view of a bi-filar single layer coil inductor having both of its filars provided with electrically insulating jackets.

FIG. 5 is an isometric view of another multi-filar coil inductor configuration similar to the multi-filar coil inductor 160b of FIG. 4, except the bi-filar single layer coil inductor 160c of FIG. 5 has a pair of helically wound filars 195a, 195b that both have electrical insulation jackets 205a, 205b. As indicated in FIG. 5, each helically wound filar 195a, 195b has an electrically conductive core 200a, 200b and an electrical insulation layer 205a, 205b.

As shown in FIG. 5, the pair of helically wound filars 195a, 195b form a plurality of coils 210a, 210b, which form the coiled portion 215 of the coil inductor 160c. The coils 210a, 210b may define a center cylindrical space that receives the barrel portion of the bobbin 155 when the coil inductor 160c is wound about the barrel portion of the bobbin 155, as indicated in FIG. 2.

As illustrated in FIG. 5, each helically wound filar 195a, 195b terminates on the proximal end of the coil inductor 160c as proximal straight filar segments 185a, 185b, which are joined together via joining material 220, for example, a weld, solder, braze or electrically conductive epoxy, to form a unified single-piece proximal straight filar segment 185. Similarly, each helically wound filar 195a, 195b terminates on the distal end of the coil inductor 160c as distal straight filar segments 190a, 190b, which are joined together via joining material 220, for example, a weld, solder, braze or electrically conductive epoxy, to form a unified single-piece distal straight filar segment 190. The unified single-piece proximal and distal straight filar segments 185, 190 extend through the respective proximal and distal portions of the bobbin 155 to respectively electrically couple to the coupler 125 and the helix base 170, as discussed above with respect to FIG. 2.

As indicated in FIG. 5, the respective extents of the insulated filars 195a, 195b extending through the respective coils 210a, 210b of the coiled portion 215 are jacketed by respective electrical insulation layers 205a, 205b, and the respective extents of the insulated filars 195a, 195b forming the respective proximal and distal straight segments 185a, 185b, 190a, 190b are un-insulated such that the respective electrically conductive cores 200a, 200b are exposed. The coils 210a, 210b of the insulated filars 195a, 195b alternate with respect to position in the coiled inductor 160c. The insulation layers 205a, 205b of the insulated filars 195a, 195b electrically isolate the conductor cores 200a, 200b from each other and from themselves.

The preceding discussion regarding the multi-filar coil inductor 160c depicted in FIG. 5 was given in the context of the multi-filar coil inductor 160c being a bi-filar single layer coil inductor 160c. However, in some embodiments, the multi-filar coil inductor 160c of FIG. 5 may have three filars, four filars or more filars, the filars being helically wound, alternatingly located in the helical coil, joined at their respective proximal and distal straight filar segments, and all insulated, as discussed above.

Figure 6:
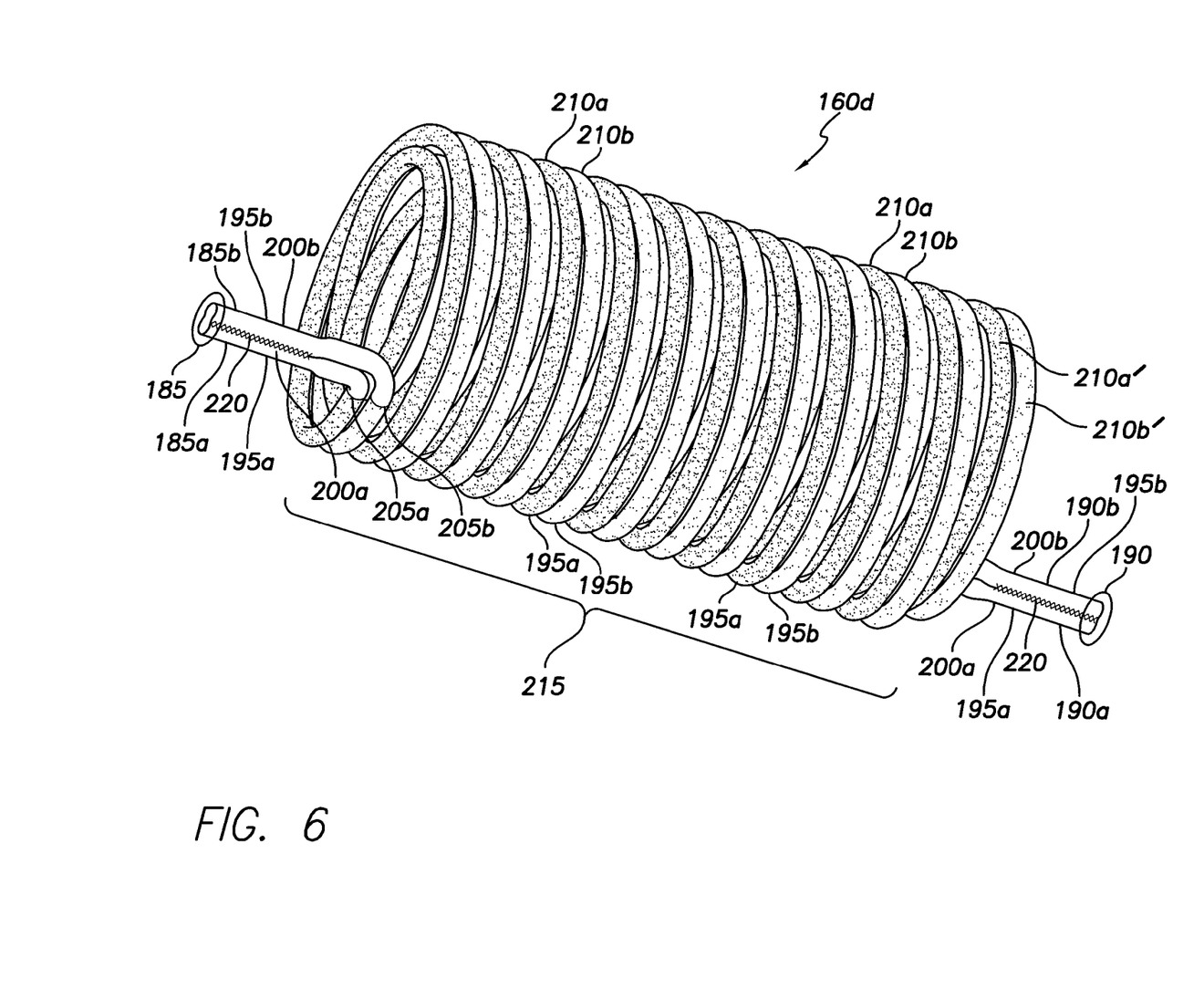
FIG. 6 is an isometric view of a bi-filar multi-layer coil inductor.

FIG. 6 is an isometric view of another multi-filar coil inductor configuration similar to the multi-filar coil inductor 160c of FIG. 5, except the coil inductor 160 is a bi-filar multi-layer coil inductor 160d. FIG. 7 is a longitudinal cross-section of the coil inductor 160d of FIG. 6. As indicated in FIGS. 6 and 7, each helically wound filar 195a, 195b has an electrically conductive core 200a, 200b and an electrical insulation layer 205a, 205b. Also, the coil inductor 160d may have three layers 225a, 225b, 225c.

Figure 7:
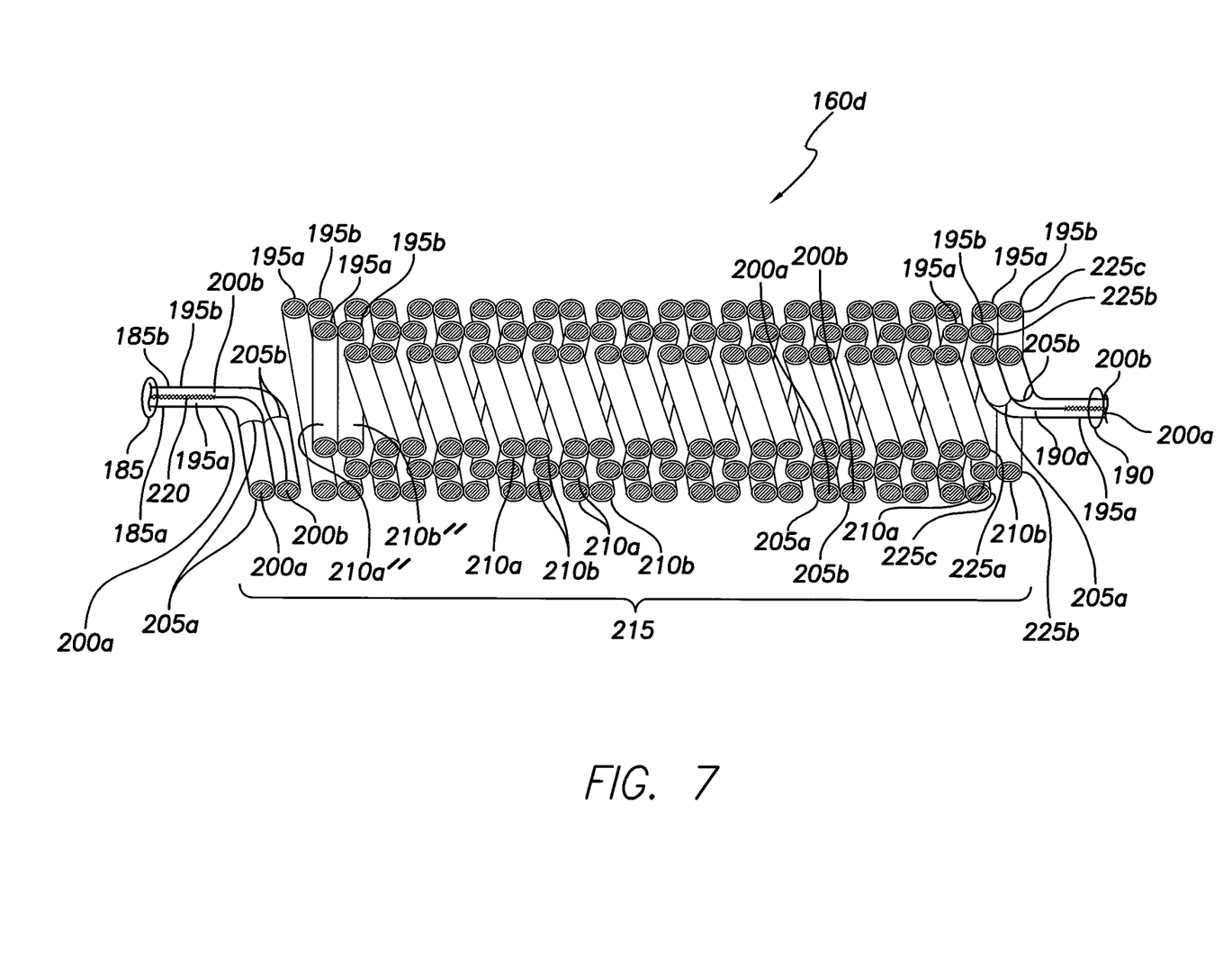
FIG. 7 is a longitudinal cross-section of the coil inductor of FIG. 6.

As shown in FIGS. 6 and 7, the pair of helically wound filars 195a, 195b form a plurality of coils 210a, 210b, which form the coiled portion 215 of the coil inductor 160d. The coils 210a, 210b of the inner layer 225a may define a center cylindrical space that receives the barrel portion of the bobbin 155 when the coil inductor 160d is wound about the barrel portion of the bobbin 155, as indicated in FIG. 2.

As illustrated in FIGS. 6 and 7, each helically wound filar 195a, 195b terminates on the proximal end of the coil inductor 160d as proximal straight filar segments 185a, 185b, which are joined together via joining material 220, for example, a weld, solder, braze or electrically conductive epoxy, to form a unified single-piece proximal straight filar segment 185. Similarly, each helically wound filar 195a, 195b terminates on the distal end of the coil inductor 160d as distal straight filar segments 190a, 190b, which are joined together via joining material 220, for example, a weld, solder, braze or electrically conductive epoxy, to form a unified single-piece distal straight filar segment 190. The unified single-piece proximal and distal straight filar segments 185, 190 extend through the respective proximal and distal portions of the bobbin 155 to respectively electrically couple to the coupler 125 and the helix base 170, as discussed above with respect to FIG. 2.

As indicated in FIGS. 6 and 7, the respective extents of the insulated filars 195a, 195b extending through the respective coils 210a, 210b of the coiled portion 215 are jacketed by respective electrical insulation layers 205a, 205b, and the respective extents of the insulated filars 195a, 195b forming the respective proximal and distal straight segments 185a, 185b, 190a, 190b are un-insulated such that the respective electrically conductive cores 200a, 200b are exposed. The coils 210a, 210b of the insulated filars 195a, 195b alternate with respect to position in the coiled inductor 160d. The insulation layers 205a, 205b of the insulated filars 195a, 195b electrically isolate the conductor cores 200a, 200b from each other and from themselves.

As best understood from FIG. 7, the three layers 225a, 225b, 225c of the coiled inductor 160d are wound in opposite pitch directions such that the inner and outer layers 225a, 225c are wound in a first pitch direction and the intermediate layer 225b is wound in a second opposite pitch direction. The coils 210a, 210b of the inner layer 225a are surrounded by the coils 210a, 210b of the intermediate layer 225b. The coils 210a, 210b of the intermediate layer 225b are surrounded by the coils 210a, 210b of the outer layer 225c. The coils 210a, 210b of the outer layer 225c are wound in a first pitch direction moving distally from the proximal straight filar segments 185a, 185b until reaching the distal end of the coiled portion 215, where the coils 210a, 210b of the outer layer 225c transition into transition coils 210a', 210b' that extend into the intermediate layer 225b and have a generally neutral pitch. The coils 210a, 210b of the intermediate layer 225b are wound in a second pitch direction opposite the first pitch direction moving proximally from the transition coils 210a', 210b' until reaching the proximal end of the coiled portion 215, where the coils 210a, 210b of the intermediate layer transition into transition coils 210a", 210b" that extend into the inner layer 225a and have a generally neutral pitch. The coils 210a, 210b of the inner layer 225a are wound in the first pitch direction moving distally from the transition coils 210a", 210b" until reaching the distal end of the coiled portion 215, where the coils 210a, 210b of the inner layer 225a extend into the distal straight filar segments 190a, 190b.

The preceding discussion regarding the multi-filar multi-layer coil inductor 160d depicted in FIGS. 6 and 7 was given in the context of the multi-filar multi-layer coil inductor 160d being a bi-filar three-layer coil inductor 160d. However, in some embodiments, the multi-filar multi-layer coil inductor 160d of FIGS. 6-7 may have three filars, four filars or more filars. Also, instead of three layers 225a, 225b, 225c, the coil inductor 160d of FIGS. 6-7 may have two layers, four layers, five layer or more layers. Even with a different number of filars and/or layers, the coiled inductor 160d of FIGS. 6-7 may have filars helically wound, alternatingly located in the helical coil, joined at their respective proximal and distal straight filar segments, and all insulated, as discussed above.

In some embodiments to facilitate the multi-filar multi-layer coil inductor having a terminal 185, 190 on each opposite end of the coil inductor, the coil inductor may have an odd number of layers, for example, three, five, seven, etc. layers. Such an odd-numbered multi-layer configuration avoids an even-numbered coil inductor configuration wherein both terminals 185, 190 are on the same end of the coil inductor, thereby possibly requiring an increased lead diameter to route an additional conductor along the coil inductor from one of the terminals 190 to the tip electrode.

In one embodiment of a multi-filar multi-layer coil inductor that may be tuned for 1.5 T or 3.0 T, the coil inductor may have 60 turns for each pair of filars in a layer and three such layers. Thus, such a bi-filar coil inductor may have 180 turns for each bi-filar pair.

In one version of the bi-filar three-layer coil inductor 160d of FIGS. 6 and 7, the coil inductor 160d employs 44 gage insulated filars 195a, 195b. The filars 195a, 195b may have electrically conductive cores 200a, 200b formed of, for example, drawn filled tubing ("DFT") wire with a higher percentage of silver for less direct current resistance ("DCR") and less stiffness, platinum wire, platinum iridium alloy wire, copper wire, etc. The insulation 205a, 205b may have a thickness of between approximately 0.0003" and 0.0005" and is formed of a material such as, for example, ETFE, PTFE, PFA, polyimide, polyurethane, etc. The resulting coiled inductor 160b may have dimensions that allow it to fit into a 6F lead header.

The embodiments discussed above with respect to FIGS. 4-7 provide a number of advantages over the embodiment discussed with respect to FIG. 3. For example, the multi-filar coil inductor circuit offers redundancy that may approximate the redundancy offered by the rest of the pacing circuit. This redundancy greatly benefits the lead reliability for over the lead's 10-year service life and the external defibrillator shock survival.

Due to the increased conductor cross-section offered by the multi-filar coiled inductor 160b, 160c, 160d as compared to the uni-filar coiled inductor 160a, the multi-filar coiled inductor 160b, 160c, 160d offers lower DC resistance than the uni-filar coiled inductor 160a, resulting in less heat generation during the large current pulse 8 A-2 ms test or the external defib shock. Also, the multi-filar coiled inductor 160b, 160c, 160d increases the heat conduction efficiency during the large current pulse 8 A-2 ms test or the external defib shock, as compared to the uni-filar coiled inductor 160a. Also, when packaged inside the lead header, there is a helix base 170 at the distal side of the coiled inductor 160, and a coupler 125 at the proximal side of the coiled inductor 160. Both the helix base 170 and the coupler 125 are of metals, such as Pt/Ir, MP35N, and can act as large heat sinks for the coiled inductor 160. The larger total cross section area of the wire metal at each terminal 185, 190 of the multi-filar coiled conductor 160b, 160c, 160d combined with the reduced number of turns or shorter length for each filar may double or triple the thermal conduction as compared to the uni-filar coiled inductor 160a.

The SRF of a multi-filar coiled lumped inductor 160b, 160c, 160d is easier to adjust to desired working frequency than a uni-filar coiled lumped inductor 160a. The parasitic inductance of a coiled lumped inductor 160 resulting from the insulation coatings is one of the two factors that define the SRF. For a uni-filar coil inductor 160a, to achieve the desired SRF of approximately 64 MHz for a 1.5 T MRI scan, five coil layers are needed when employing 44 gage wire for the filar, resulting in a lead header of at least 7F. On the other hand, the lead header may be reduced down to 6F for a bi-filar three layer coil inductor 160d employing 44 gage wire for the filars, achieving the desired SRF of approximately 64 MHz for a 1.5 T MRI scan.

For the multi-filar coiled inductors 160b, 160c, 160d, the large inductance and the SRF near the working frequency of 64 MHz or 128 MHz generate high impedance at the MRI working frequency. This filters the induced RF current and minimizes the RF heating at the lead electrode, while not adversely impacting the pacing occurring via the lead.

The inductance of the multi-filar coiled inductors 160b, 160c, 160d is not adversely impacted by the increased filar number as compared to the uni-filar coiled inductor 160a. In some embodiments as can be understood from a comparison of FIGS. 3-5, this is because the total number of coil turns are similar between the uni-filar and bi-filar coiled inductors 160a, 160b, 160c, and total number of coil turns may be one of the dominate factors for the inductance of a coiled inductor 160.

For the multi-filar multi-layered coiled inductor 160d, the small diameter insulated filars and multi-layered tight winding can save space while increasing the total number of the coil turns. Also, the insulated filars and multi-layered tight winding can result in strong electromagnetic interactions or mutual inductance and capacitance due to the skin effects. The result of the multi-filar multi-layered coiled inductor 160d is a coiled inductor 160 that offers output inductance that is essentially the same as a uni-filar coiled inductor 160a, but in a package that is substantially smaller than the uni-filar coiled inductor.

For any one or more of the coil inductor configurations discussed above with respect to FIGS. 3-7 and as can be understood from FIG. 2, the coil inductor 160 may have a coil inductor length ICL that extends between the proximal and distal extents of the coiled portion 215 of between approximately 0.02" and approximately 0.25". The coil inductor 160 may also have an coil inductor inner diameter ICID of between approximately 0.01" and approximately 0.05". The coil inductor 160 may also have an coil inductor outer diameter ICOD of between approximately 0.01" and approximately 0.125".

For any one or more of the coil inductor configurations discussed above with respect to FIGS. 3-7, the insulation layer 205 may be formed of polymer materials such as, for example, ETFE, PTFE, perfluoroalkoxy copolymer resin ("PFA"), polyimide, polyurethane, or etc. The insulation layer 205 may also have a radial thickness of between approximately 0.0001" and approximately 0.003".

For any one or more of the coil inductor configurations discussed above with respect to FIGS. 3-7, the conductive core 200 may be formed of an electrically conductive biocompatible material such as, for example, platinum, platinum-iridium alloy, MP35N, silver-cored MP35N, titanium, titanium alloy or etc. Alternatively, assuming adequate hermetic sealing of the coil inductor 160, the conductive core 200 may be formed of an electrically conductive non-biocompatible material such as, for example, copper or etc. The conductive core 200 may have a diameter of between approximately 0.0005" and approximately 0.005".

For any one or more of the coil inductor configurations discussed above with respect to FIGS. 4-7, the insulation 205a for the first filar 195a may be of a different material than the insulation 205b of the second filar 195b. For example, the insulation 205a for the first filar 195a may be of ETFE and the insulation 205b of the second filar 195b may be PTFE. Alternatively or additionally, the insulation 205a for the first filar 195a may be of a different thickness than the insulation 205b of the second filar 195b. For example, the insulation 205a for the first filar 195a may have a thickness of 0.001" and the insulation 205b of the second filar 195b may have a thickness of 0.002".

Figure 8:
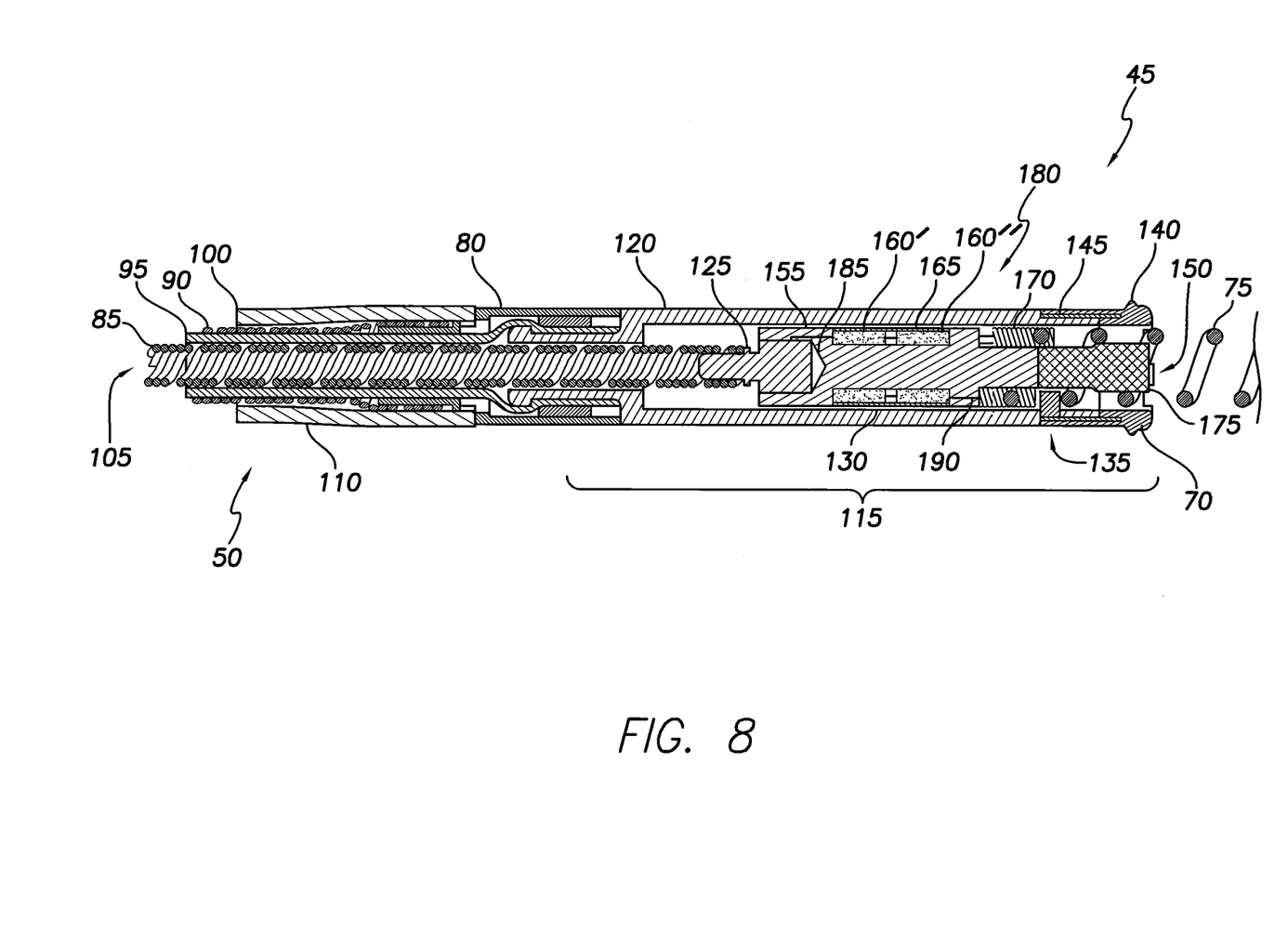
FIG. 8 is the same view as FIG. 2, except of an inductor assembly may employ two or more lumped inductors in electrically connected in series.

As can be understood from FIG. 8, which is the same view as FIG. 2, except of another embodiment, the inductor assembly 130 may employ two or more lumped inductors 160', 160" in electrically connected in series. The two or more lumped inductors 160', 160" in series may be in the form of two or more identical coiled inductors 160', 160" in series and of any one of the coiled inductor configurations discussed above with respect to FIGS. 3-7. Alternatively, the two or more lumped inductors 160', 160" in series may be in the form of two or more identical coiled inductors 160', 160" in series and of any two or more of the coiled inductor configurations discussed above with respect to FIGS. 3-7.

In one embodiment of the lead depicted in FIG. 8, one inductor 160' of the lumped inductors 160', 160" in series is configured to be tuned for a first frequency such as, for example, 64 MHz for 1.5 T MRI scans, and the other inductor 160" of the lumped inductors 160', 160" in series is configured to be tuned for a second frequency such as, for example, 128 MHz for 3.0 T MRI scans.

In some embodiments, the inductors 160 may be other types of inductors besides coiled inductors. For example, in some embodiments, the inductors 160 may be printed circuit inductors, embedded circuit inductors, or multi-layer inductors. In some embodiments, a single inductor 160 may actually be formed of multiple types of inductors such as coil type inductors, multi-layer type inductors, embedded circuit inductors and printed circuit type inductors.

Although the present invention has been described with reference to preferred embodiments, persons skilled in the art will recognize that changes may be made in form and detail without departing from the spirit and scope of the invention.

What is claimed is:
1. An implantable medical lead comprising:
   a body including a distal portion with an electrode and a proximal portion with a lead connector end; and
   an electrical pathway extending between the electrode and lead connector end and including a single coiled inductor including first and second electrically conductive filar cores and a lead conductor electrically coupled between the lead connector end and the single coiled inductor, wherein the first and second filar cores are electrically coupled together at a proximal terminal on a proximal end of the coiled inductor, the first and second filar cores are electrically coupled together at a distal terminal on a distal end of the coiled inductor, and wherein the first and second filar cores are helically wound together into a coiled portion to form at least a portion of the single coiled inductor between the proximal and distal terminals, the filar cores being electrically isolated from each other in the coiled portion, wherein the proximal terminal is located distal of the lead connector end and is electrically coupled to a distal end of the lead conductor, the lead conductor being electrically coupled to the lead connector end, and the distal terminal located proximal of the electrode is electrically coupled to a portion of the electrical pathway extending to the electrode.

2. The lead of claim 1, wherein the first filar core is encased within an electrical insulation layer in the coiled portion and the second filar core is at least partially free of an electrical insulation layer in the coiled portion.

3. The lead of claim 1, wherein the first filar core is encased within a first electrical insulation layer in the coiled portion and the second filar core is encased within a second electrical insulation layer in the coiled portion.

4. The lead of claim 3, wherein a material of the first insulation layer is different from a material of the second insulation layer.

5. The lead of claim 3, wherein a thickness of the first insulation layer is different from a thickness of the second insulation layer.

6. The lead of claim 3, wherein the coiled portion includes multiple helical coil layers formed of the helically wound first and second filar cores.

7. The lead of claim 6, wherein a first coil layer of the multiple helical coil layers is wound with a first pitch and a second coil layer of the multiple helical coil layers is wound with a second pitch opposite the first pitch.

8. The lead of claim 7, wherein the second coil layer is immediately surrounding the first coil layer.

9. The lead of claim 1, wherein the first and second filar cores in the coiled portion each form a series of respective coils and the coils of the first filar core and the coils of the second filar are arranged in an alternating fashion along a length of the coiled portion.

10. The lead of claim 1, wherein the first and second cores are physically joined into a unified single piece distal and proximal terminals via at least one of welding, brazing, soldering, and electrically conductive epoxy.

11. The lead of claim 1, further including a header assembly enclosing the coiled inductor.

12. An implantable medical lead comprising:
a lead body including an electrode at a distal portion of the lead body and a lead connector end at a proximal portion of the lead body;
an electrical pathway extending between the electrode and the lead connector end including a lead conductor forming a segment of the electrical pathway; and
a single coiled inductor forming a segment of the electrical pathway wherein the single coiled inductor is formed of multiple filars helically wound together to form at least a portion of a coiled portion of the single coiled inductor, wherein the multiple filars are electrically insulated from each other along the coiled portion and electrically coupled at proximal and distal ends of the multiple filars the proximal end of multiple filars being electrically coupled to a distal end of the lead conductor, the lead conductor being electrically coupled to a lead connector the distal end of the multiple filars being proximal of the electrode and being electrically coupled to the electrode.

13. The lead of claim 12, wherein the multiple filars are helically wound in an alternating fashion so coils of a first helically wound filar of the multiple filars and coils of a second helically wound filar of the multiple filars are alternatingly located in the helical coil.

14. The lead of claim 12, wherein at least one of the multiple filars is encased within an electrical insulation layer in the coiled portion and at least another one of the multiple filars is at least partially free of an electrical insulation layer in the coiled portion.

15. The lead of claim 12, wherein all of the multiple filars are encased within an electrical insulation material.

16. The lead of claim 12, wherein a material of a first insulation layer for at least one of the multiple filars is different from a material of a second insulation layer for another at least one of the multiple filars.

17. The lead of claim 12, wherein a thickness of a first insulation layer for at least one of the multiple filars is different from a thickness of a second insulation layer for another at least one of the multiple filars.

18. The lead of claim 12, wherein the multiple filars is at least one of 2, 3, 4, 5, and 6 filars.

19. The lead of claim 12, wherein the multiple filars is at least two filars.

20. The lead of claim 12, wherein the coiled portion includes multiple helical coil layers formed of the helically wound multiple filars.

21. The lead of claim 20, wherein the multiple helical coil layers is at least one 2, 3, 4, 5 and 6 layers.

22. The lead of claim 20, wherein the multiple helical coil layers is at least two layers.

23. The lead of claim 20, wherein at least one of the multiple helical coil layers is wound with a first pitch and a second coil layer of the multiple helical coil layers is wound with a second pitch opposite the first pitch.

24. The lead of claim 23, wherein the second coil layer is immediately surrounding the first coil layer.

25. The lead of claim 12, wherein the proximal and distal ends of the multiple filars are physically joined into respective unified single piece distal and proximal terminals via at least one of welding, brazing, soldering, and electrically conductive epoxy.

26. The lead of claim 12, wherein the coiled inductor includes a first inductor tuned for a first frequency and a second inductor tuned for a second frequency different from the first frequency.

27. The lead of claim 26, wherein the first frequency is 64 MHz and the second frequency is 128 MHz.

* * * * *